United States Patent [19]

Thielcke

[11] 3,957,859
[45] May 18, 1976

[54] PROCESS FOR THE PRODUCTION OF AROMATIC SULFONATES

[75] Inventor: George W. Thielcke, Southport, Conn.

[73] Assignee: King Industries, Inc., Norwalk, Conn.

[22] Filed: May 8, 1973

[21] Appl. No.: 358,312

[52] U.S. Cl............................ 260/505 P; 260/505 C
[51] Int. Cl.² ....................................... C07C 143/24
[58] Field of Search .......... 260/505 S, 505 P, 505 C

[56] References Cited
UNITED STATES PATENTS

| | | | |
|---|---|---|---|
| 2,764,548 | 9/1956 | King et al. | 260/505 |
| 2,802,866 | 8/1957 | Salzmann et al. | 260/505 |
| 2,843,626 | 7/1958 | Gebelein et al. | 260/505 |
| 2,844,624 | 7/1958 | Bloch | 260/505 |
| 3,075,005 | 1/1963 | Garden et al. | 260/505 |

Primary Examiner—James O. Thomas, Jr.
Assistant Examiner—A. Siegel
Attorney, Agent, or Firm—Morgan, Finnegan, Pine, Foley & Lee

[57] ABSTRACT

Aromatic sulfonates having, respectively, preferential oil-, and water- and alcohol-solubility are prepared by reacting aromatic compounds and sulfuric acid in a medium capable of liquid-liquid extraction with water; the product stream is then subjected to countercurrent extraction against water in a first multi-stage column; the water stream is next subjected to countercurrent extraction against a water-immiscible higher alcohol in a second multi-stage column; and the sulfonate having preferential water- and alcohol-solubility, which has transferred from the product stream, to the water stream, and finally to the higher alcohol, is recovered from the latter as the free acid or as a salt thereof. The process is especially adapted to the production of dinonylnaphthalene disulfonic acid.

6 Claims, 2 Drawing Figures

PROCESS FOR THE PRODUCTION OF AROMATIC SULFONATES

This invention relates to a process for the preparation of sulfonated organic compounds. More particularly, it is concerned with a process for the production of sulfonates by reacting an aromatic compound with sulfuric acid in a solvent, and with a novel multi-state liquid-liquid countercurrent extraction process sequence for recovering the sulfonate having preferential water- and higher alcohol-solubility, or a derivative thereof, in substantially pure form.

BACKGROUND OF THE INVENTION

It is often desirable to produce sulfonates by reacting an aromatic compound with sulfuric acid. In many cases, this provides two or more aromatic sulfonates, at least one of which is preferentially oil soluble and at least one of which is preferentially water soluble. In U.S. Pat. No. 2,764,548, which is owned by the assignee of the present application, there is described a process for the production of dinonylnaphthalene monosulfonates. The salts of the monosulfonates are relatively highly soluble in oils, and form compositions having exceptional rust-inhibiting properties. It is also disclosed in the patent that the sulfonation of dinonylnaphthalene with sulfuric acid also produces the corresponding disulfonic acid, and this is described to be accumulated in an aqueous, spent acid layer which is later separated and discarded. Because under common commerical conditions the predominant product is the monosulfonate, the disulfonate has been treated as a byproduct, and wasted. In connection with this, disposal of this wasted product has been an economic and environmental problem because of a tendency to deteriorate the quality of water into which the waste is dispersed. It has now been found that dinonylnaphthalene disulfonic acid is useful in its own right, for example, as a textile processing surfactant and as a wetting agent. In particular, the salts of the disulfonic acid are useful as hydrotropes, in that they help to make clear solutions of petroleum or hydrocarbon solvents in water. The disulfonic acid is also useful in metal and equipment degreasing in combination with water only or as an additive for steam. A somewhat analogous problem is encountered in the sulfonation of didodecylnaphthalene, and also in the corresponding benzene analogs.

It is an objective of the present invention to provide a novel means of countercurrently washing and extracting a reaction mixture of an aromatic compound, sulfuric acid and a solvent to isolate a sulfonate, which, in the case of dinonylnaphthalene disulfonic acid, was formerly discarded a waste e product, in pure forms and thus provide new marketable items. It is an important feature of this invention, that the waste acid layer in U.S. Pat. No. 2,764,548 is treated in such a way that the valuable disulfonic acid product can be recovered, while at the same time upgrading the quality of the spent acid layer to a degree where it can be safely disposed of by addition to environmental waters. Of course, other sulfonation processes will also benefit from the present invention.

DESCRIPTION OF THHE INVENTION

Figure 1:
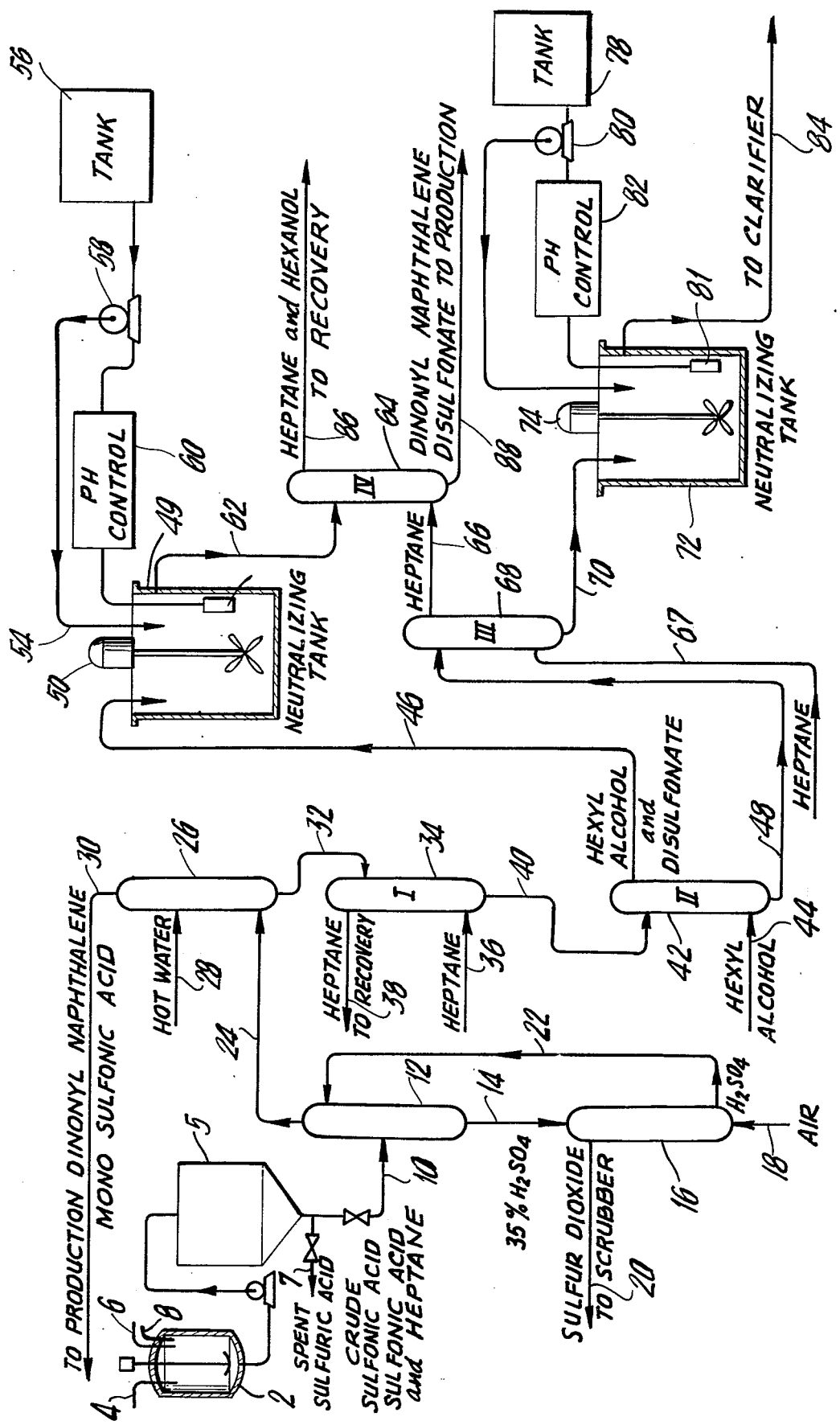
In FIG. 1 is illustrated, in flow diagram form, the arrangement of a typical production unit in which one aspect of the process of this invention may be carried out.

According to the present invention, there is provided a process for the production of two or more aromatic sulfonates, at least one of which is preferentially oil soluble and at least one of which is preferentially water soluble and, more preferentially, higher alcohol soluble, said process comprising agitating a mixture of an aromatic compound, sulfuric acid and a solvent, the improvement which comprises:

a. carrying out the reaction in a solution capable of liquid-liquid extraction with water;

b. passing the reaction solution through a multi-stage reaction column countercurrently to a stream of water to produce an aqueous solution of said preferentially water soluble and, more preferentially, higher alochol soluble sulfonate;

c. passing said aqueous solution through a multi-stage extraction column countercurrently to a stream of higher alcohol to produce a solution of the preferentially water soluble and more preferentially, higher alcohol soluble sulfonate in said higher alcohol; and d. recovering the preferentially water soluble and, more preferentially, higher alcohol soluble sulfonate from said solution.

According to a preferred aspect of this invention, there is provided a process for the production of dinonylnaphthalene disulfonic acid by agitating a mixture of dinonylnaphthalene, sulfuric acid and a solvent, in which the improvement comprises:

a. carrying out the reaction in a solution capable of liquid-liquid extraction with water;

b. separating the layers and passing the organic solution through a multi-stage extraction column countercurrently to a stream of water to produce an aqueous solution of dinonylnaphthalene disulfonic acid capable of liquid-liquid extraction with a higher alcohol;

c. passing the aqueous solution through a multi-stage extraction column countercurrently to a stream of higher alcohol to produce a solution of dinonylnaphthalene disulfonic acid in the higher alcohol; and d. recovering the dinonylnaphthalene disulfonic acid or salt thereof from said solution.

Those skilled in the art of sulfonation are well aware that aromatic organic substrates, such as benzene and its analogs, e.g., alkylbenzenes, toluene, the xylenes, polyalkylbenzenes, and higher alkyl mono and di-and polysubstituted benzenes, such an nonyl and decyl and dodecyl, straight and branched chain-substituted benzenes and the corresponding naphthalenes, form sulfonates which are preferentially oil soluble (selectively extractable with organic hydrocarbon solvents, and the like), and sulfonates which are preferentially water soluble (and alcohol soluble, being selectively extractable with water and alcohols, and the like). These are separated from one another by the present process in its broadest aspects.

As in the case in U.S. Pat. No. 2,764,548, which is incorporated herein by reference, it is also a preferred feature of this invention to use a dinonylnaphthalene, the nonyl radicals of which are highly branched, and to use as the reaction solvent, a water-immiscible material selected from naphtha, hexane, heptane, octane, chlorinated hydrocarbons and the like. Procedures to make the starting materials are thoroughly described in the '548 patent. Another preferred feature of the invention is to use as higher alcohol in the countercurrent extraction, one which contains from about 5 to about 12 carbon atoms, and, preferably, a pentanol, hexanol, heptanol, octanol, nonanol, decanol and the like. Mixed or primary alcohols are especially useful.

While the present invention has wide application, it will be described, for convenience sake, with reference to dinonylnaphthalene.

By way of illustration, dinonylnaphthalene disulfonic acid is formed (along with dinonylnaphthalene monosulfonic acid which, as is mentioned above, is the oil-soluble component) by agitating a mixture of dinonylnaphthalene, sulfuric acid and a solvent such as petroleum naphtha, hexane, heptane, octane, and chlorinated solvents. The use of a solvent for the dinonylnaphthalene during the sulfonation reaction is necessary to maintain the reaction in the liquid state, so that the sulfuric acid and the dinonylnaphthalene may be thoroughly mixed during the sulfuric acid addition and the heat of reaction controlled. Moreover, at completion, the presence of solvent in sufficient quantities maintains both of the sulfonic acids in the liquid state and facilitates separation of the spent acid layer from the organic layer containing the dinonylnaphthalene monosulfonic acid.

In carrying out step (a), sulfuric acid, preferably oleum, is introduced into the agitated solution of dinonylnaphthalene at the desired temperature. By way of illustration, the temperature of the solution will have been adjusted to about 60° to 70°F., then 20% oleum will be added over a period of from about 4 to 5 hours, keeping the temperature below about 70°F., with external cooling. After the acid has been added, the batch is then warmed to about 80°F. and agitated for about 1 hour more. This produces a reaction solution which contains dinonylnaphthalene disulfonic acid, together with dinonylnaphthalene monosulfonic acid, small amounts of various impurities, and unreacted starting materials. The product of this process separates into two phases, an upper, organic layer and a lower, spent acid layer which is returned to the oleum supplier for reprocessing.

To remove some of the byproduct sulfur compounds, the separated organic layer, before being subjected to the first step of the present process, can be treated with e.g., 35% sulfuric acid and the sulfuric acid layer can be blown with air to produce sulfur dioxide which is removed in a conventional scrubber. This optional feature will be described later.

In the next stage of the present process, the organic product stream of crude sulfonic acids, with some by-products, is passed through a multi-stage extraction column countercurrently to a stream of water, preferably hot water, to produce an aqueous stream of dinonylnaphthalene disulfonic acid, and an organic stream enriched in dinonylnaphthalene monosulfonic acid. The extraction column can be of any conventional design and materials of construction, but due regard must be taken to the relatively acidic natures of the materials being handled.

With respect to the geometry of the column and the feed rate and other parameters, as should be obvious to those skilled in the art, the ratio of product stream introduced to water introduced into the multi-stage extraction column will be dependent upon a number of factors, such as the partition co-efficient of dinonylnaphthalene disulfonic acid between the respective liquid phases, the concentration of materials in the various streams, the temperatures, the column packing, and the like. There are several advantages to using a high ratio of product stream to aqueous stream in any given extraction. First, a smaller volume of aqueous extractant will result in a higher concentration of dinonylnaphthalene disulfonic acid in the aqueous stream leaving the column and this will facilitate subsequent steps. In addition, because the capacity of a given column will depend upon the combined flow of light and heavy phases, a lower volume of the aqueous phase will permit a higher flow rate of the product solution. On the other hand, a very high phase ratio will result in poor dispersion and poor mass transfer.

It has been found important, for highest efficiency, to heat the water before admitting it to the column. In general, the temperature of the water, as introduced, can range from 130° to 190°F., but preferably the water is admitted at a temperature in the range of 160° to 170°F. With respect to flow ratios, when using water at a temperature in the range of 130° to 170°F., it is desirable that the ratio of the reaction phase being fed to the water being fed vary between 2:1 and 1:1 with the higher ratios being used at lower concentrations of the dinonylnaphthalene disulfonic acid in the product stream.

Following the liquid-liquid extraction with water in the first step, the organic eluant contains almost all of the dinonylnaphthalene monosulfonic acid, and this is sent to production for recovery by conventional means, e.g., as described in U.S. Pat. No. 2,764,548. The aqueous stream from the column, which is enriched in dinonylnaphthalene disulfonic acid, is then sent to another multi-stage extraction column where it is passed countercurrently to a stream of a waterimmiscible or substantially water-immiscible higher alcohol, preferably one containing from about 5 to about 12 carbon atoms, straight chained or branched chain, primary, secondary or tertiary, the carbon atoms being alkyl, arylalkyl, or alkylaryl as pentanol, hexanol, heptanol, decanol, benzyl alcohol, paramethylbenzyl alcohol and the like. The geometry of the column, the flow ratios and the materials of construction will all be selected having the above-enumerated considerations in mind.

In preferred features of this invention, the aqueous solution of the dinonylnaphthalene disulfonic acid will first be treated with a stream of a solvent to remove any entrained organic soluble material, before going to the "higher alcohol column". For example, the water solution of dinonylnaphthalene disulfonic acid will be passed through an intermediate multi-stage extraction column countercurrently to a stream of such a solvent, such as naphtha, hexane, heptane, octane and the like, and preferably the solvent used in the reaction, to strip out small amounts of any entrained monosulfonic acid, unreacted dinonylnaphthalene, organic sulfates, and the like.

Moreover, in another preferred feature, after the hexyl alcohol extraction, the aqueous effluent from that column may also be liquid-liquid extracted with such a solvent, and another column to recover any entrained higher alcohol thus aiding the process economics. This can be done by passing the aqueous effluent into a multi-stage reaction column countercurrently to a stream of the same type of solvent, e.g., naphtha, hexane, heptane and octane, used before. To preserve the environment, the aqueous effluent from this column can be neutralized, such as by treatment with a precipitant, e.g., a lime slurry, to cause inorganic materials to be precipitated. After settling, the supernatant liquid can be dispersed in streams, rivers, estuarys, and the like, without adverse effect.

Returning to the process of the invention, following liquid-liquid extraction of the dinonylnaphthalene disulfonic acid into the higher alcohol, the product acid will be recovered from the higher alcohol solution by conventional means, such as concentration or by conversion to a salt. In the latter case, neutralization with a suitable metal hydroxide, oxide or carbonate, e.g., a compound of sodium, potassium, calcium, magnesium, barium, zinc and the like will produce a solution of the corresponding metal salt of dinonylnaphthalene disulfonic acid. Because of their excellent surface active properties, at this stage, the salts will produce a homogeneous mixture of water, the higher alcohol and the salt. Concentration of this mixture will cause the salt to separate and it can be recovered. Preferably, however, the higher alcohol will be removed, e.g., by selective extraction with a water immiscible solvent. This leaves a solution of the desired salt in water. For some purposes, this will be a marketable item. Removal of the water will also leave the product salt as a residue.

DESCRIPTION OF THE PREFERRED EMBODIMENTS

Referring to FIG. 1, Reactor 2 is fitted with an agitator, coils for cooling and heating and conduits 4, 6 and 8, for introduction, respectively, of dinonylnaphthalene, solvent, and sulfuric acid. Illustratively, 1,000 lbs. of petroleum naphtha (heptane) or equivalent solvent is charged through conduit 6. Then 1,000 lbs. of dinonylnaphthalene is added through conduit 4 and the agitator is started. The temperature of the solution is adjusted to from 60° to 70°F. and, next, 1,100 lbs. of 20% oleum is added through conduit 8 over a period of from 4 to 5 hours, keeping the temperature below 70°F. After the acid has been added, the batch is warmed to 80°F. and agitated for about 1 hour more. The batch is now pumped to settling tank 5, e.g., one large enough to hold one or two such batches. The lower, spent acid layer, containing approximately 85% sulfuric acid and impurities is withdrawn through conduit 7 and, if desired, returned to the oleum supplier for reprocessing. The upper layer, containing the mono- and di-sulfonic acids, some sulfur dioxide and some sulfuric acid in heptane, is now drawn through conduit 10 into the middle of liquid-liquid extraction column 12 and the solution of crude sulfonic acids in heptane leaves the top of column 12 while sulfuric acid of 30–45% concentration is admitted through conduit 22 to pass downwardly therethrough removing excess sulfuric acid, and the sulfur dioxide then exits through conduit 14 into gas liquid contacter 16, where countercurrent air is introduced through conduit 18 to mix therewith and remove sulfur dioxide. The gas and entrained impurities leave through conduit 20 and a scrubber (not shown) removes sulfur dioxide. The "airblown" sulfuric acid is recycled to column 12 through conduit 22.

The solution of crude sulfonic acids in the organic solvent is then transferred through conduit 24 into liquid-liquid extraction column 26 where it is brought into contact with heated water entering through conduit 28 and the co-produced dinonylnaphthalene monosulfonic acid leaves the top of column 26 as a solution in organic solvent through conduit 30. This is sent to production for isolation, formulation, storage and sale.

Because the density of water exceeds the density of the solution of dinonylnaphthalene mono- and di- sulfonic acids in most solvents, the aqueous solution descends through column 26 dissolving the dinonylnaphthalene disulfonic acid and this leaves the bottom of the column through conduit 32. If, for example, the solvent density is greater than that of water, e.g., if methylene chloride or chloroform is used, obviously the flow directions will be reversed, but suitable piping will be obvious to those skilled in this art.

Next, the aqueous stream is sent into countercurrent contact in column 34 against an upwardly rising stream of heptane or similar solvent which is introduced at the bottom through conduit 36 and leaves through the upper conduit 38 wherefrom it is sent to recovery. This is an optional step, but enhances process economics. The effluent from the bottom of column 34, exiting through conduit 40, is an aqueous solution of dinonylnaphthalene disulfonic acid which is then fed to countercurrent extraction column 42 where it is brought into intimate contact with an upwardly rising stream of a higher alcohol, such as hexyl alcohol. The alcohol is introduced at the lower part of column 42 through conduit 44, selectively extracts the dinonylnaphthalene disulfonic acid, and leaves the upper part of column 42 through conduit 46.

Exiting from the lower part of column 42 through conduit 48 is the aqueous phase substantially depleted in the disulfonate. This is waste and will ultimately be discarded, after treatment to recover entrained higher alcohol and possibly toxic impurities.

The product stream exiting from column 42 through conduit 46 is sent to neutralizing tank 49 which is fitted with agitator 50, pH sensing device 52 and conduit 54 for introduction of an aqueous solution of a metal hydroxide, oxide or carbonate, e.g., sodium hydroxide, which is made up in holding tank 56 and transferred through pump 58 in response to a signal sent by pH controller 60. In neutralizing tank 49, dinonylnaphthalene disulfonic acid is converted to the corresponding metal salt, and a homogeneous product stream comprising an aqueous solution of this salt and the higher alcohol is removed from tank 49 through conduit 62 to liquid-liquid extraction column 64 where it descends downwardly against an upwardly flowing organic stream, e.g., heptane, introduced through conduit 66.

In a preferred embodiment, the heptane or other organic solvent, will comprise an effluent leaving liquid-liquid extraction column 68. Such an optional column is provided to treat the downwardly flowing spent aqueous solution from column 42, to recover entrained higher alcohol. The effluent from column 68 is removed through conduit 70 and, before being discarded, is treated with a precipitant in neutralizing tank 72, fitted with agitator 74, pH sensor 76 and, like the neutralizing system above-described, a corresponding holding tank 78, pump 80, pH sensor 81 and ph controller 82. The precipitant, e.g., lime slurry, will precipitate impurities residing in the aqueous phase. The dispersion is sent through conduit 84 to a settling tank or other clarifier (not shown), and the clear liquid can be discarded in streams or rivers without deleterious effects.

The organic solvent and higher alkanol leaving column 64 through conduit 86 can be sent, e.g., to a steam still, for recovery and reuse.

The product of the process, dinonylnaphthalene disulfonate, leaves column 64 through conduit 88 as an aqueous solution and can be sent to production. In the process described this will comprise an aqueous solution of the disodium salt at any convenient concentration, commonly 40% by weight. In one manner of recovering the product, this solution can be dried in a drum dryer, spray dryer, or the like, and this leaves the disodium salt as a pale tan powder.

Figure 2:
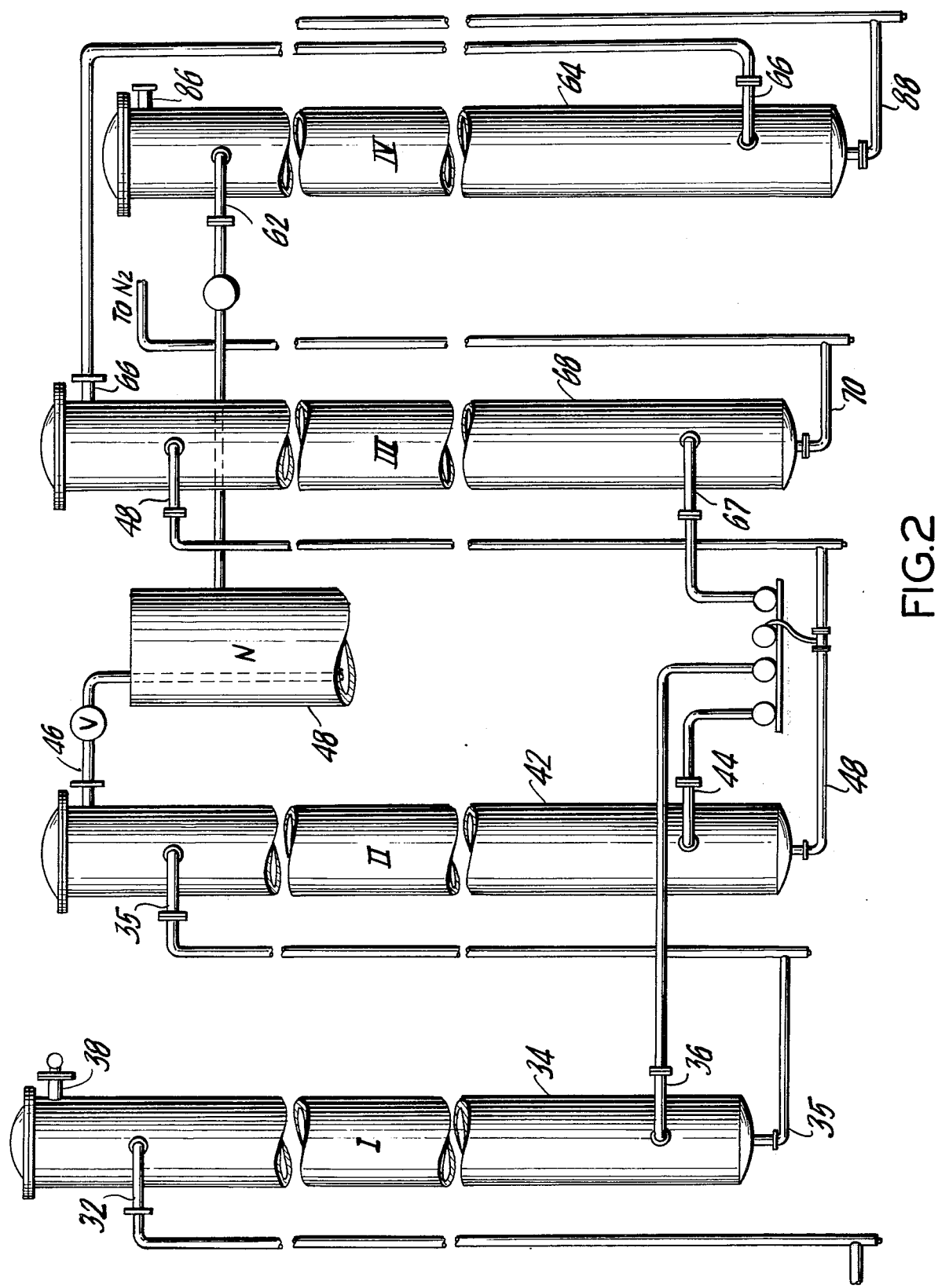
FIG. 2 is an elevation view in partial section illustrating a compact arrangement, suitable for a chemical plant, of four of the multi-stage liquid-liquid extraction columns laid out in FIG. 1, with their piping.

To further illustrate the process of the invention, a series of extraction separations were carried out using a product feed solution containing about 5% of dinonylnaphthalene disulfonic acid, 40% of dinonylnaphthalene monosulfonic acid, 4% sulfuric acid, 47% of heptane and various impurities, mainly 1% sulfur dioxide and 3% unsulfonated residue. The extraction columns were arranged as shown in FIG. 2.

Columns 34, 42, 68 and 64 are 18 inches in diameter with a packed section of about 12 feet high. They include separating sections of about 2 feet in height above and below the packed section. To simplify this description, columns 12 and 26 of FIG. 1 are not shown, but these are of the same size and construction. Column 12, however, has an upper, phase separation section of about 4 feet in height. In columns 34, 42, 68 and 64, the light phase is introduced centrally through respective conduits 36, 44, 67 and 66 and nozzles 2 feet from the bottom, then discharged from side nozzles 3 inches from the top through respective conduits 38, 46, 66 and 86. The heavy phase is introduced centrally just above the packed section through respective conduits 32, 35, 48 and 62, and discharged from nozzles in the dished bottoms through conduits 35, 48, 70 and 88, respectively.

The columns can be made of any suitable material, but in this instance, from a fiber-glass polyester composition designated "Bonate MRC-82" by the manufacturer, Beetle Plastics. The resin is Atlac-382. The columns are packed with ceramic saddles (Intalox, Norton Co.). The internals, such as support plates and holddown plates are also ceramic, except for column 64 which has polypropylene saddles and support plate. Chlorinated polyvinyl chloride piping (CPVC) is very suitable for such a system.

The following operational results are typical:

Product feed solution at approximately 150 gal./hr. is fed to column 12 against 35% sulfuric acid at about 90 gal./hr. The function of this column is to remove sulfur dioxide, and as much sulfuric acid as possible, for resale as 40% acid.

The feed analyzes 0.93% sulfur dioxide, and the raffinate, 0.06%, thus showing 93.5% removal. The sulfuric exits at 0.915% sulfur dioxide, and is reduced to 0.034% in air blower 16 before being recycled. The sulfuric acid is reduced from about 4% to about 1%. The concentrations of disulfonic and monosulfonic acids are not affected.

In column 26, the product stream is run countercurrently to hot (170°F.) water at the same rate. The exiting water phase has a normality of 0.384, of which the sulfuric acid normality is 0.195, indicating the water has removed 5.10% disulfonic acid and 0.95% sulfuric acid from the crude. Analysis of the raffinate shows only 0.78% residual disulfonic acid, indicating 85% removal.

The aqueous phase from the preceding operation, after extraction with heptane in column 34, is visually clear, and shows no light phase on centrifuging. Thus, any entrained product (oily) layer has been completely removed.

The aqueous stream is then run countercurrently in column 42 against 1-hexanol entering at about 85 gal./hr. The normality of the aqueous stream is 0.384 on entering this column, 0.215 on exiting. Since the sulfuric acid normality is 0.195, the percent removal of disulfonic acid is: (0.384−0.215)/(0.384−0.195)×100, or 89%. The residual disulfonic acid is reduced to 0.56%.

The aqueous stream is run countercurrently in column 68 to heptane at about 120–130 gal./hr. The hexanol in the aqueous phase is reduced to 0.36 %. This effluent, now containing essentially only sulfuric acid, is run to neutralizer 72, to be neutralized with lime and settled. The clear supernatant liquid is run to waste, the gypsum, to drying beds, for eventual land fill.

The alcohol extract from column 42 has a normality of 0.272, indicating 7.3% disulfonic acid; it contains 91% hexanol, the balance being water. After neutralization with 20% sodium hydroxide in the continuous neutralizer 49, it flows to the top of column 64 where it flows countercurrent to the heptane from column 68, the latter being the continuous phase. The mixed solvents exiting from the top of this column are 39% hexanol, 61% heptane, as determined from the specific gravity. The product exiting from the bottom of the column contains 26% solids and 58% hexanol, indicating that only 69% of the hexanol has been removed in this column. The remainder of the hexanol is removed, and the solids concentrated to about 40% by distillation in a still. Preferably, this still will be a continuous steam still.

Typical data obtained from stripper column 12 are illustrated in Table 1:

Table 1

| Stripper Column Efficiency | | | |
|---|---|---|---|
| Run No. | 1 | 2 | 3 |
| % sulfur dioxide in feed | 0.930 | 0.800 | 0.366 |
| % sulfur dioxide in raff. | 0.061 | 0.085 | 0.041 |
| % sulfur dioxide removed | 0.869 | 0.715 | 0.325 |
| column efficiency | 93.4% | 89.4% | 88.8% |
| % $SO_2$ in exiting sulfuric | 0.915 | 0.879 | 0.412 |
| % $SO_2$ in entering sulfuric | 0.034 | 0.042 | 0.017 |
| % $SO_2$ removed in stripper | 0.881 | 0.837 | 0.395 |
| stripper efficiency | 91.5% | 95.2% | 95.9% |

It is desirable to remove any sulfur dioxide to prevent the formation of an unfilterable precipitate, e.g., if the monosulfonic acid is eventually neutralized with barium or calcium oxide or carbonate. Usually, any small residual amount of sulfur dioxide is removed in column 26 along with the disulfonic acid.

The efficiency of column 42 in removing the disulfonic acid from the aqueous phase is, of course, highly dependent on the relative feed rate of the alochol, while the efficiency of column 64 in removing the residual higher alcohol from the aqueous phase is dependent on the relative rate of heptane feed to this column. Both are favored by higher temperatures. These facts may be illustrated by the data in Table 2:

Table 2

| | | | Relative solv.flow | | Efficiency | |
|---|---|---|---|---|---|---|
| Run No. | Temp. °C. | Aqu.flow gal./hr. | Hexanol | Heptane | Col.42 | Col.64 |
| 3 | 25 | 130 | .29 | .49 | 57% | 43% |
| 4 | 33 | 180 | .51 | .78 | 85% | 68% |
| 5 | 38 | 144 | .69 | .53 | 92% | 68% |

Efficiency of Columns 42 and 64

Run No. 3 shows the cumulative bad effects of low temperature operation and low solvent flow. The other two runs show improved efficiency in both columns, due to higher operating temperature and higher solvent flow rates.

The above description and results demonstrate that the process of this invention produces a valuable material, dinonylnaphthalene disulfonic acid, which was formerly a waste product, in the form of a marketable item. Moreover, the effluent previously discarded, containing 3 to 4% of organic disulfonates, now contains less than 1% of this material and may safely be dispersed in environmental waters.

The procedure and apparatus as described above are used, except that didodecylnaphthalene is used instead of dinonylnaphthalene. Didodecylnaphthalene disulfonic acid is recovered from the higher alcohol and didodecylnaphthalene monosulfonic acid is recovered from the heptane after countercurrent extraction of the disulfonate with the hot water.

Although the above embodiments have shown various modifications of the present invention, other variations are possible in the light of the above teachings. It is therefore to be understood that changes may be made in the particular embodiments of the invention described which are within the full intended scope of the invention as defined by the appended claims.

I claim:

1. In a process for the production of dinonylnaphthalene monosulfonic acid and dinonylnaphthalene disulfonic acid by agitating a mixture of dinonylnaphthalene, sulfuric acid and a solvent, said monosulfonic acid being preferentially soluble in a solvent selected from the group consisting of naphtha, hexane, heptane and octane and said disulfonic acid being preferentially soluble in water and more soluble in a higher alkanol containing from about 5 to about 12 carbon atoms than in water, the improvement which comprises:
   a. carrying out the reaction in a solvent selected from the group consisting of naphtha, hexane, heptane and octane;
   b. passing the reaction solution through a multi-stage reaction column countercurrently to a stream of water to produce an aqueous solution of dinonylnaphthalene disulfonic acid by extraction from the reaction solution;
   c. passing said aqueous solution through a multi-stage extraction column countercurrently to a stream of a higher alkanol containing from about 5 to about 12 carbon atoms to produce a solution of dinonylnaphthalene disulfonic acid in the higher alkanol by extraction from said aqueous solution; and
   d. recovering dinonylnaphthalene disulfonic acid from said alkanol solution.

2. A process as defined in claim 1 including the step of recovering dinonylnaphthalene monosulfonic acid from the reaction solution after countercurrent extraction with water in step (b).

3. A process as defined in claim 1 wherein the higher alkanol is selected from the group consisting of pentanol, hexanol, heptanol, octanol, nonanol and decanol.

4. A process as defined in claim 1 wherein the solvent for the reaction solution in heptane and the higher alkanol is hexanol.

5. A process as defined in claim 1 wherein the product is recovered from solution in said higher alkanol by adding thereto a water solution of a metal selected from the group consisting of sodium, potassium, calcium, magnesium, barium, and zinc in the form of a compound selected from the group consisting of hydroxide, oxide and carbonate to form an aqueous solution of the corresponding metal salt of dinonylnaphthalene disulfonic acid.

6. A process as defined in claim 5 including the step of passing the aqueous solution of the corresponding metal salt of dinonylnaphthalene disulfonic acid through a multi-stage extraction column countercurrently to a stream of a solvent selected from the group consisting of naphtha, hexane, heptane and octane to selectively extract any entrained higher alkanol.

* * * * *